US009642575B2

(12) United States Patent
Freeman et al.

(10) Patent No.: US 9,642,575 B2
(45) Date of Patent: May 9, 2017

(54) ECG NOISE REDUCTION SYSTEM FOR REMOVAL OF VEHICLE MOTION ARTIFACT

(71) Applicant: ZOLL Medical Corporation, Chelmsford, MA (US)

(72) Inventors: Gary A. Freeman, Chelmsford, MA (US); Ulrich R. Herken, Chelmsford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 219 days.

(21) Appl. No.: 14/216,225

(22) Filed: Mar. 17, 2014

(65) Prior Publication Data

US 2014/0288450 A1   Sep. 25, 2014

Related U.S. Application Data

(60) Provisional application No. 61/799,467, filed on Mar. 15, 2013.

(51) Int. Cl.
*A61B 5/00*       (2006.01)
*A61B 5/0402*   (2006.01)
*A61B 5/04*       (2006.01)

(52) U.S. Cl.
CPC .......... *A61B 5/6893* (2013.01); *A61B 5/0402* (2013.01); *A61B 5/04012* (2013.01); *A61B 5/721* (2013.01); *A61B 5/725* (2013.01); *A61B 5/04017* (2013.01); *A61B 2560/0247* (2013.01); *A61B 2562/0219* (2013.01)

(58) Field of Classification Search
CPC .......................... A61B 5/6893; A61B 5/04012
USPC ............................................. 600/509; 601/41
See application file for complete search history.

(56) References Cited

U.S. PATENT DOCUMENTS

| | | |
|---|---|---|
| 4,059,099 A | 11/1977 | Davis |
| 4,088,138 A | 5/1978 | Diack et al. |
| 4,296,755 A | 10/1981 | Judell |
| 4,355,634 A | 10/1982 | Kanter |
| 4,588,383 A | 5/1986 | Parker et al. |
| 4,610,254 A | 9/1986 | Morgan et al. |
| 4,619,265 A | 10/1986 | Morgan et al. |
| 4,680,708 A | 7/1987 | Ambos et al. |
| 4,863,385 A | 9/1989 | Pierce |
| 4,928,674 A | 5/1990 | Halperin et al. |
| 5,077,667 A | 12/1991 | Brown et al. |
| 5,092,341 A | 3/1992 | Kelen |
| 5,109,862 A | 5/1992 | Kelen et al. |
| 5,247,945 A | 9/1993 | Heinze et al. |
| 5,285,792 A | 2/1994 | Sjoquist et al. |
| 5,391,187 A | 2/1995 | Freeman |
| 5,466,244 A | 11/1995 | Morgan |
| 5,474,574 A | 12/1995 | Payne et al. |
| 5,496,257 A | 3/1996 | Kelly |
| 5,511,553 A | 4/1996 | Segalowitz |
| 5,562,710 A | 10/1996 | Olsen et al. |
| 5,589,639 A | 12/1996 | Antonio et al. |
| 5,591,213 A | 1/1997 | Morgan |
| 5,611,815 A | 3/1997 | Cole et al. |

(Continued)

*Primary Examiner* — Nadia A Mahmood
(74) *Attorney, Agent, or Firm* — ZOLL Medical Corporation (57) ABSTRACT

An ECG processing system which removes vehicle motion artifact from a measured ECG signal based on vehicle cabin motion and vehicle suspension motion.

29 Claims, 4 Drawing Sheets

(56) References Cited

U.S. PATENT DOCUMENTS

| | | | |
|---|---|---|---|
| 5,617,853 A | 4/1997 | Morgan | |
| 5,619,265 A | 4/1997 | Suzuki et al. | |
| 5,645,571 A | 7/1997 | Olson et al. | |
| 5,662,690 A | 9/1997 | Cole et al. | |
| 5,683,424 A | 11/1997 | Brown et al. | |
| 5,700,281 A | 12/1997 | Brewer et al. | |
| 5,735,879 A | 4/1998 | Gliner et al. | |
| 5,755,671 A | 5/1998 | Albrecht et al. | |
| 5,957,856 A | 9/1999 | Weil et al. | |
| 6,125,299 A | 9/2000 | Groenke et al. | |
| 6,171,257 B1 | 1/2001 | Weil et al. | |
| 6,174,295 B1 | 1/2001 | Cantrell et al. | |
| 6,178,357 B1 | 1/2001 | Gliner et al. | |
| 6,201,992 B1 | 3/2001 | Freeman | |
| 6,224,562 B1 | 5/2001 | Lurie et al. | |
| 6,246,907 B1 | 6/2001 | Lin et al. | |
| 6,263,238 B1 | 7/2001 | Brewer et al. | |
| 6,306,107 B1 | 10/2001 | Myklebust et al. | |
| 6,308,094 B1 | 10/2001 | Shusterman et al. | |
| 6,351,671 B1 | 2/2002 | Myklebust et al. | |
| 6,390,996 B1 | 5/2002 | Halperin et al. | |
| 6,393,316 B1 | 5/2002 | Gillberg et al. | |
| 6,418,342 B1 | 7/2002 | Owen et al. | |
| 6,427,685 B1 | 8/2002 | Ray, II | |
| 6,438,419 B1 | 8/2002 | Callaway et al. | |
| 6,496,731 B1 | 12/2002 | Lovett | |
| 6,597,943 B2 | 7/2003 | Taha et al. | |
| 6,658,290 B1 | 12/2003 | Lin et al. | |
| 6,671,545 B2 | 12/2003 | Fincke | |
| 6,687,540 B2 | 2/2004 | Marcovecchio | |
| 6,827,695 B2 | 12/2004 | Palazzolo et al. | |
| 6,865,413 B2 | 3/2005 | Halperin et al. | |
| 6,872,080 B2 | 3/2005 | Pastrick et al. | |
| 6,961,612 B2 | 11/2005 | Elghazzawi et al. | |
| 7,183,930 B2 | 2/2007 | Basir et al. | |
| 7,220,235 B2 | 5/2007 | Geheb et al. | |
| 7,822,471 B2 | 10/2010 | Bowers | |
| 2001/0047140 A1 | 11/2001 | Freeman | |
| 2002/0026131 A1 | 2/2002 | Halperin | |
| 2002/0055694 A1 | 5/2002 | Halperin et al. | |
| 2002/0165471 A1* | 11/2002 | Halperin | A61B 5/04017 601/41 |
| 2002/0165585 A1 | 11/2002 | Dupelle et al. | |
| 2002/0193711 A1 | 12/2002 | Halperin et al. | |
| 2005/0027416 A1* | 2/2005 | Basir | A61B 5/02455 701/36 |
| 2006/0025825 A1* | 2/2006 | Bowers | A61B 5/046 607/5 |
| 2007/0142735 A1 | 6/2007 | Shin et al. | |
| 2009/0112135 A1 | 4/2009 | Palazzolo | |
| 2010/0016685 A1 | 1/2010 | Muehlsteff et al. | |

* cited by examiner

ECG NOISE REDUCTION SYSTEM FOR REMOVAL OF VEHICLE MOTION ARTIFACT

This application claims priority to U.S. Provisional Application 61/799,467 filed Mar. 15, 2013.

FIELD OF THE INVENTION

The methods and devices described below relate to the field of cardio-pulmonary resuscitation (CPR).

BACKGROUND OF THE INVENTIONS

The ECG (electrocardiogram) of a patient may be used to diagnose various problems with the patient's heart. In the context of sudden cardiac arrest, the ECG can be used to determine if the patient is in fibrillation, and, if so, if the patient's heart is susceptible to defibrillation. Using the ECG, a doctor or an AED (automatic external defibrillator) can determine whether the ECG signal represents a normal sinus rhythm or an abnormal rhythm that may be reset by administration of a defibrillating shock. The ECG signal is subject to several sources of noise. ECG signals are currently processed with digital filters to reduce noise due to other physiological sources (muscles, EGG, EMG, etc.), and nearby electrical equipment.

Halperin, et al., ECG Signal Processor and Method, U.S. Pat. No. 6,865,413 (Mar. 22, 2005) disclosed an ECG processing system which eliminates noise caused by the chest compression provided by a rescuer or chest compression device. The system includes ECG sensors (electrodes) for measuring the ECG signal of a patient, an accelerometer for producing an acceleration signal indicative of the displacement of a chest of a patient, and a processor operatively connected to the accelerometer and to the ECG sensor. The processors uses the acceleration signal to identify noise in the ECG signal. The processor processes the acceleration signal and the measured ECG signal to produces an output comprising an estimated true ECG signal. The system and method is used in ZOLL Medical's See-Thru CPR® feature of its AED Pro® automated external defibrillators.

In addition to these noise sources, the patient may be subject to motion of a vehicle used to transport the patient to a hospital. This motion may lead to noise and artifact in the ECG signal measured from the patient. We refer to this artifact as vehicle motion artifact. This noise can substantial, and may result in a measured ECG which is too noisy to be analyzed with confidence. The noise may be caused by motion of the patient and gurney over terrain, or motion of an ambulance or other conveyance used to transport the patient. Transport can be lengthy, so that a patient cannot be properly assessed for extended periods of time. Inability to assess the ECG may lead to loss of valuable diagnostic data and failure to apply defibrillating shock when appropriate.

SUMMARY

The devices and methods described below provide for more accurate determination of an actual ECG from a patient, where the ECG is taken from a patient subject to vehicle motion which may impart vehicle motion artifacts to the measured ECG. Vehicle motion artifact, which presents as noise in the measured ECG of the patient, is identified by measuring vehicle motion, and using the measured vehicle motion as an aid to identifying the resultant artifact. The predicted artifact is then subtracted from the measured ECG signal to obtain an estimated true ECG which is suitable for analysis by doctors and automatic defibrillators to determine is defibrillating shock is appropriate. The vehicle motion can be determined from motion sensors on the vehicle, which may be mounted on the vehicle cabin and/or the vehicle suspension. In the case of vehicle cabin motion, the motion is expected to match the motion of the patient. In the case of vehicle suspension motion, the motion is expected to occur slightly before resultant cabin motion, and thus anticipate or predict the motion of the patient. The vehicle suspension motion can be used to predict and identify vehicle motion artifact in the measured ECG of the patient, and that artifact can be removed to provide an ECG that more closely matches the actual ECG of the patient.

DETAILED DESCRIPTION OF THE INVENTIONS

Figure 1:
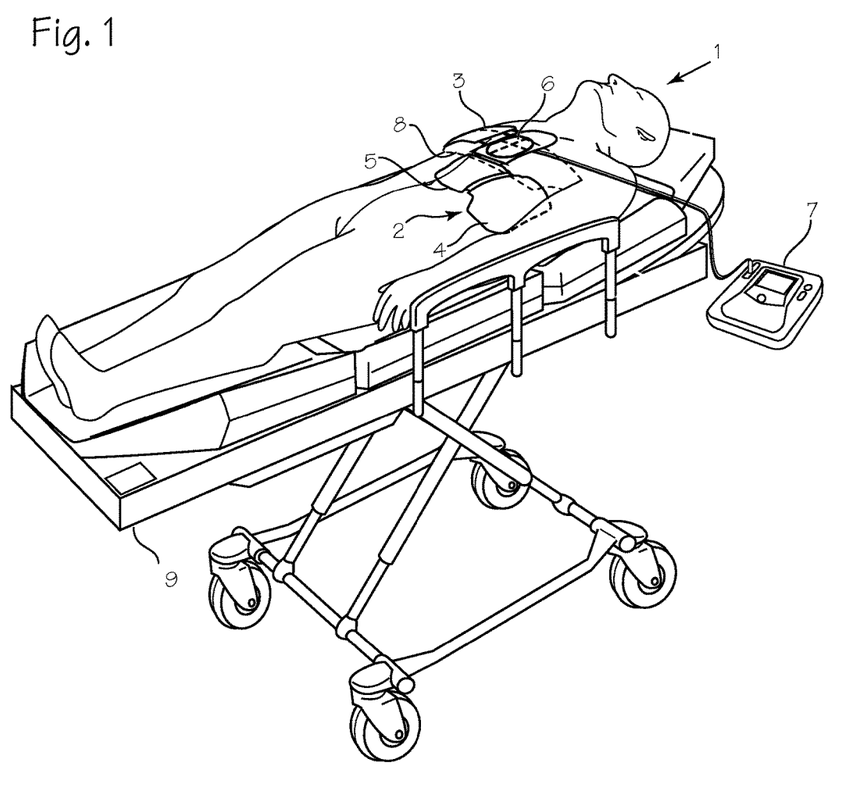
FIG. 1 illustrates a typical cardiac arrest victim fitted with an ECG electrode assembly.

FIG. 1 illustrates a typical cardiac arrest victim 1 fitted with an ECG electrode assembly 2. The electrode assembly includes electrodes adapted for both detecting the ECG of the cardiac arrest victim and for delivery of cardioverting shock to the patient. As illustrated in this view, the ECG electrode assembly 2 is disposed on the patient's chest. This assembly includes the sternum electrode 3, the apex electrode 4, the sternal bridge 5 and the chest compression monitor 6. The sternal and apex electrodes are used to detect the ECG of the patient, and to deliver shock. An associated ECG processor 7, which may be a stand-alone ECG monitor, or may combined with a manual defibrillator or automatic defibrillator (AED), is operably connected to the electrodes. The ECG processor provides a means for processing the ECG signal as described below. It receives ECG signals from the electrodes, and processes those signals to generate a signal representing the ECG waveform. This signal may be presented on a display for interpretation by a doctor, or it may communicated to an automatic defibrillator for automatic analysis by a computer within the AED. The chest compression monitor serves to detect chest compressions for use in scrubbing the ECG of CPR induced artifact as disclosed in Halperin, and also to measure depth of compressions for any CPR compression performed on the patient. A chest compression belt 8 (shown in phantom) of a chest compression device may be applied to the patient, and operated as described in Mollenauer, Modular CPR Assist Device, U.S. Pat. No. 6,066,106 (May 23, 2000).

The patient is disposed on a gurney 9, which is typically used to transport patients.

Figure 2:
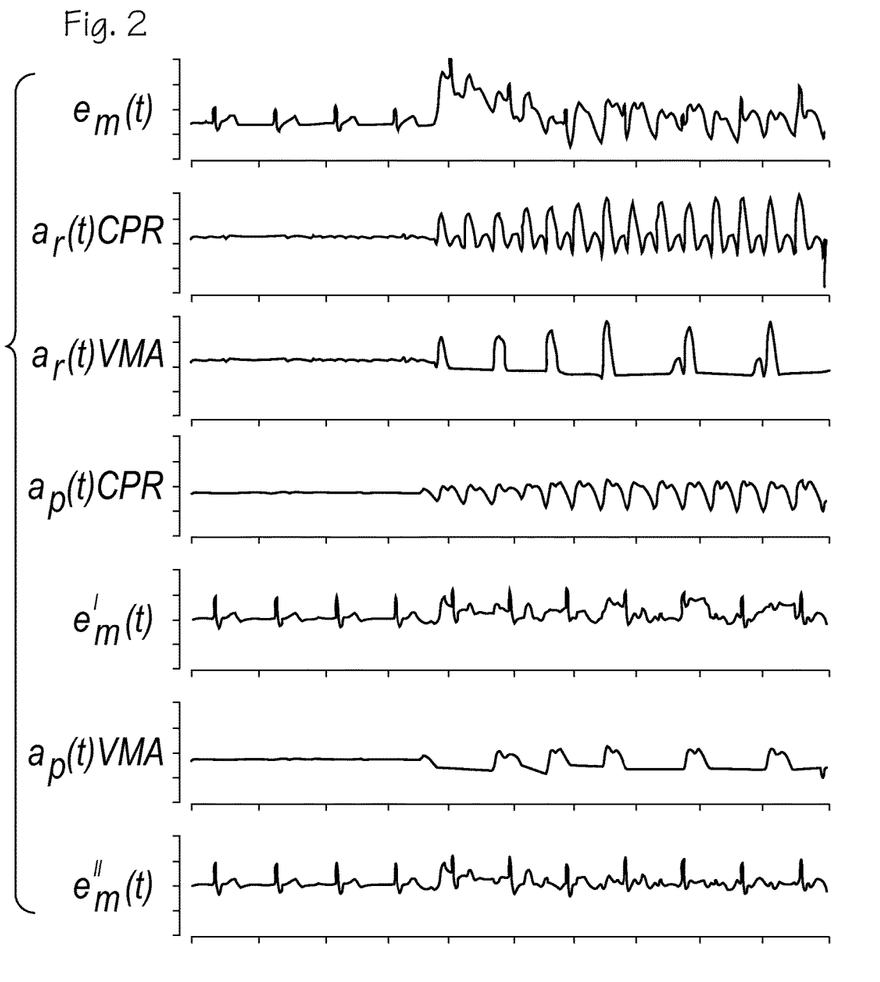
FIG. 2 shows several waveforms pertinent to the processing of a ECG signal corrupted with noise.

FIG. 2 shows several waveforms pertinent to the processing of ECG signal corrupted with noise, including waveforms $e_m(t)$, $a_r(t)$, $a_p(t)$, $e'_m(t)$ and $e''_m(t)$. The first waveform $e_m(t)$ represents the measured ECG signal of a cardiac arrest victim. This waveform may be corrupted with various noise sources, such as electronic noise from environmental sources (nearby equipment and power sources, noise from other electrical activity in the patient's body, etc.), and noise induced by mechanical motions such as CPR motion and vehicle motion. For the purpose of this disclosure, $e_m(t)$ can be taken as an ECG waveform after processing to remove environmental noise (noise from nearby power sources, for example), but may contain CPR induced artifact and vehicle motion artifact. The waveforms $a_r(t)CPR$ and $a_r(t)VMA$ represent motion sensor signals (acceleration signals, for example) as measured at the patient's chest (for CPR) and as measured by sensors mounted on the vehicle or gurney for detection of vehicle motion which may lead to vehicle motion artifact (VMA). The following waveform $a_p(t)CPR$ is the predicted artifact that might be created by CPR motion. The waveform $a_p(t)VMA$ is the predicted artifact that might be created by vehicle motion. The next waveform $e'_m(t)$, is the processed ECG signal, which has been processed to remove the CPR-induced artifact from the measured ECG $e_m(t)$. The waveform $e'_m(t)$ is achieved using the method described in Halperin, U.S. Pat. No. 6,390,996 or comparable methods. Absent vehicle motion artifact, this signal is sufficient for clinical use. However, if vehicle motion artifact is significant, the ECG waveform must be further processed to obtain waveform $e''_m(t)VMA$, which has been scrubbed of vehicle motion artifact represented by waveform $a_p(t)VMA$. Waveform $e'''_m(t)VMA$ is an estimated true ECG from which vehicle motion artifact has been removed.

Figure 3:
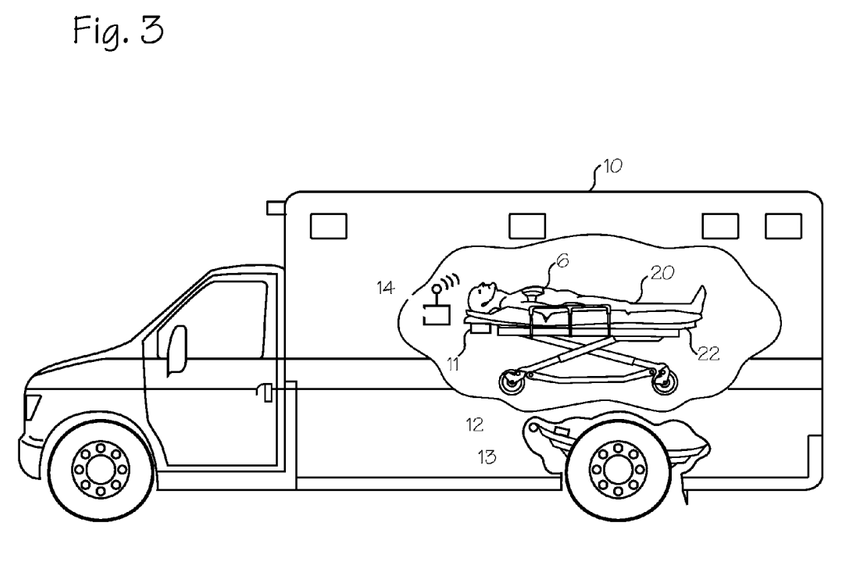
FIG. 3 illustrates placement of accelerometers to detect vehicle motion which may lead to vehicle motion artifact in the measured ECG of the patient.

The waveform $a_p(t)CPR$ is obtained from the accelerometer disposed on the patient's chest. This accelerometer signal may also include acceleration of the vehicle in which the patient is transported. (Accelerometers signals are provided by the chest compression monitor, but the system may instead use a waveform from any motion sensor.) The waveform $a_p(t)VMA$ (or several such waveforms) is obtained from accelerometers or motion sensors, which are mounted on the vehicle in which the patient is transported, as shown in the following figure.

FIG. 3 illustrates placement of accelerometers to detect vehicle motion which may lead to vehicle motion artifact in the measured ECG of the patient. As illustrated, the patient 1 is disposed on the gurney 9 within an ambulance 10. One or more motion sensors 11 are disposed on the gurney, or on the ambulance housing, or any other surface that moves in lock-step with the patient, or on several of these components. (The conveyance is illustrated as an ambulance, but the method and system apply to any vehicle or conveyance.) A motion sensor 12 is disposed on a component of the vehicle suspension 13 (such as a leaf spring, coil spring, shock absorber, strut, axle, air spring, steering rack, linkage, arm, torsion beam, sway bar, any other suspension component or any bushing, boot, etc. associated with a suspension component). Again, several such sensors may be employed on several such components. These components are expected to move (typically up and down) in response to the surface features on the road on which the ambulance is driven. Thus, the motion sensors can detect motions, such as vehicle acceleration and deceleration, jarring motion due to road impacts, or rumbling motion of the gurney over rough and bumpy surfaces. The motion may be periodic, as from travel over roadway seams, or random, as from occasional impacts with roadway bumps. Motion signals from suspension components will indicate motion which may also detected by vehicle cabin sensors (sensors fixed to the vehicle cabin) of patient/gurney sensors after dampening and transmission of that motion through the vehicle suspension system.

The motion signal from the sensors on the suspension may be communicated wirelessly or through a wired connection to the ECG processor 7. The signals can be passed through a transceiver 14, which can be a wireless transceiver or wired transceiver, interconnecting the various motion sensors and the ECG processor.

The motion sensors comprise accelerometers, velocity sensors, vibration transducers and equivalent sensors. Motion sensors for detecting vehicle suspension motion may include these sensors, and additionally may include proximity sensors, infrared or RF motion detectors, ultrasound motion detectors, etc., mounted on the frame of the vehicle and operable to detect relative motion between the frame and the suspension components. Each of these means for sensing motion may be used to acquire signals corresponding to vehicle cabin motion, gurney motion, or vehicle suspension motion. The means for acquiring the measured ECG signal include the electrodes. The chest compression monitor serves as a means for acquiring and providing a signal indicative of a CPR-induced artifact. As currently practiced, the chest compression monitor employs accelerometers, but can also be cased on velocity sensors, distance sensors, magnetic sensors, and any other mechanism from which the timing of chest compressions can be determined.

The motion sensors are used to generate a model of the noise that leads to artifacts in the measured ECG signal. The model may incorporate noise components from the vehicle and from chest compressions. The noise model may be used to predict the artifact, or to estimate the artifact, and the computer system within the ECG processor may be programmed to subtract the noise, as predicted or estimated, from the measured ECG signal to eliminate the artifacts and output an estimated true ECG signal.

Figure 4:
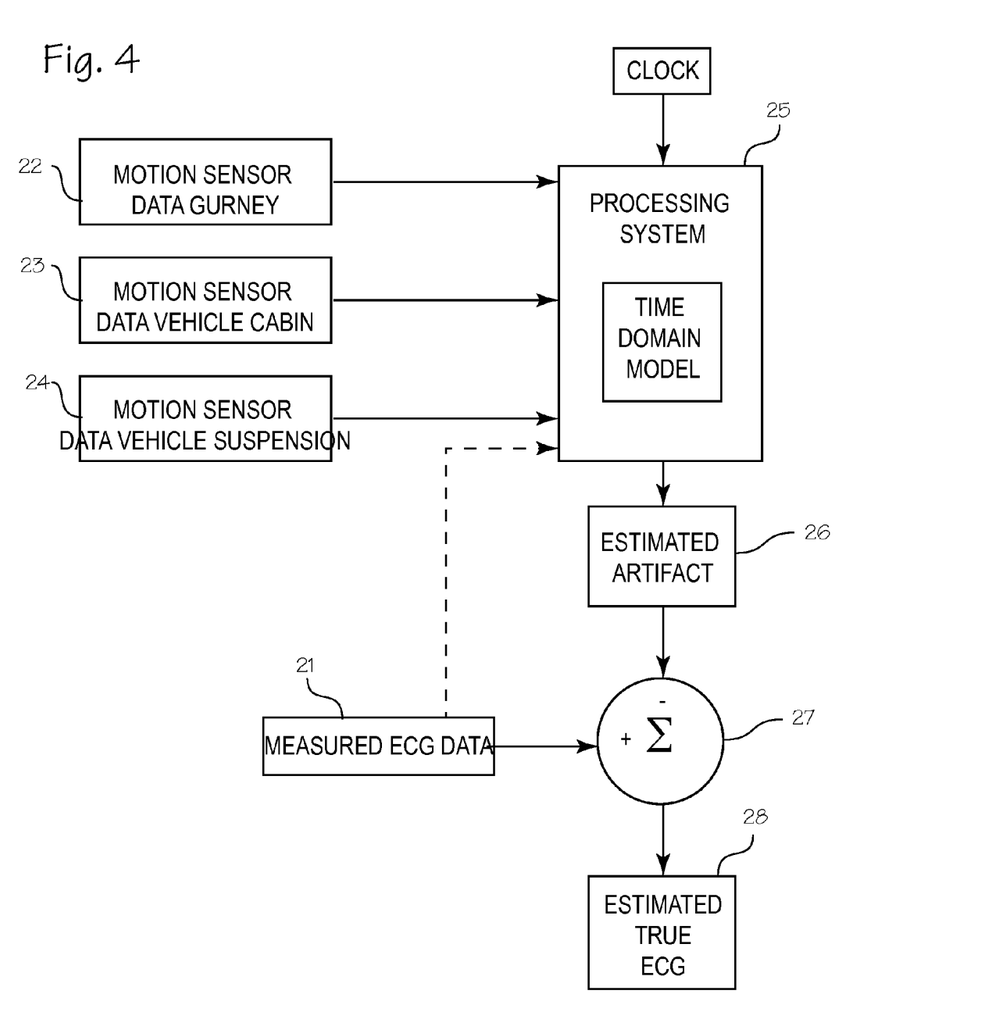
FIG. 4 illustrates the algorithm for processing the measured ECG signal into an estimated true ECG signal.

FIG. 4 illustrates the algorithm for processing the measured ECG signal into an estimated true ECG signal. This algorithm is described with reference to a measured ECG that is not corrupted with CPR noise, either because the patient is not subject to CPR compression or because the CPR-induced artifact has been removed. Nonetheless, the processing necessary for removal of vehicle motion artifact may be performed before or after (or coincident with) the processing necessary for removal of CPR-induced artifact. Motion data (typically, acceleration signal from an accelerometer or velocity signal from a velocity sensor) is input from various sensors which detect gurney motion, vehicle cabin motion, and vehicle suspension motion. The input into the processor includes the measured ECG, or $e_m(t)$, (item 21) and various signals associated with noise inducing events, including patient/gurney mounted motion sensor signals 22, vehicle cabin motion signals 23 from cabin mounted sensors and vehicle suspension motion signals 24. Vehicle suspension motion signals may be used with or without vehicle cabin motion signals, and vice-versa. The motion signals are input to the ECG processor to be processed to provide a model of the noise created by the various noise sources in model processor (item 25). This step results in output of an estimated or predicted artifact $a_p(t)VMA$ (item 26). At this point, the measured ECG $e_m(t)$ is combined with the estimated artifact $a_p(t)VMA$ to produce an estimated true ECG, $e''_m(t)$. The estimated artifact has been removed in the signal combiner 27. The output of the algorithm, as performed by the ECG processor, is the estimated true ECG $e''_m(t)$ waveform (item 28). (The CPR-induced artifact can be processed along with the several motion sensor signals, with input regarding the signal indicative of the CPR-induced artifact along with the motion sensor signals 22,23 and 24, or, as mentioned above, it can be removed prior to the steps illustrated in FIG. 4, with the measured ECG data (item 21) being replaced with ECG scrubbed of CPR-induced artifact, or it can be removed from the output of signal combiner 27.)

The various motion sensor inputs are processed by the ECG processor at step 25 (the ECG processor component that builds and applies the model). The estimated artifact can be created using a model which reflects the effects of each source of noise, either alone or in combination. A time-domain or frequency domain model may be adapted to account for effects of each noise source by comparing the motion sensor data input from each source to identify noise components each sensor location. The model identifies a linear or non-linear system that transforms the motion signals $a_r$ into waveforms composed of artifactual components $a_p$ in the measured ECG $e_m$. Once this system is identified, the artifactual component can be predicted, using predictive filtering by taking the output $a_p$, using the measured motion signal $a_r$ as the input. When the predicted signal $a_p$ is subtracted from the measured ECG $e_m$, this results in the estimated true ECG $e''_m$. This method may be implemented using each of the motion inputs alone, or in combination with the others.

Motion sensor data from motion sensors mounted on vehicle suspension can be expected to report vehicle motion in anticipation of related motion of the vehicle cabin or the gurney which are both expected to move in tandem with the patient. That is, motion signals from suspension components will indicate motion which may also detected by vehicle cabin sensors (sensors fixed to the vehicle cabin) of patient/gurney sensors after dampening and transmission of that motion through the vehicle suspension system. The motion sensor data from the vehicle suspension components is thus predictive of noise in the measured ECG signal. This noise may be somewhat rhythmic, or entirely arrhythmic, and may be injected into the vehicle suspension/vehicle cabin system a few milliseconds before causing movement of the cabin or gurney which causes motion artifact in the ECG. This system can be modeled to account for the delay in transmission of vibrations from the suspension components to the vehicle cabin and or gurney, and thus the ECG electrodes on the patient. Thus, in the ECG processor, the estimated artifact is created using a model which reflects the delay in transmission of vehicle suspension component motion to the ECG electrodes to impart noise into the measured ECG, and the model is applied to the measure vehicle suspension motion to create the estimated artifact $a_p(t)$VMA(suspension).

The system used to accomplish the ECG noise reduction includes an ECG processor, the various motion sensors, and ECG electrodes on the patient, and the desired output device, which may be an ECG monitor with its display, an automatic external defibrillator with its display and associated computer system which analyzes the estimated true ECG, or a manual defibrillator with its display. The ECG processor comprises a computer system with one or more microprocessors, memory including a computer program code configured to cause the computer system to operate by receiving signals corresponding to the various inputs, processing the inputs, and outputting the estimated true ECG, or signal representing the estimated true ECG, to a display and/or additional computer system components for analysis. Thus, the ECG processing system is programmed to accomplished the methods and algorithms described above. The various noise sources may be addressed singly or in combination, and the benefits of each method may be obtained with or without also incorporating the remaining methods. For example, the system may be operated to obtain the benefits of removing vehicle cabin motion artifact without analyzing motion artifact arising from vehicle suspension motion, and the system may be operated to obtain the benefits of removing artifact based on vehicle suspension motion sensors without analyzing motion artifact arising from motion of the vehicle cabin or gurney. The method may also be implemented in tandem with, or independently of, CPR motion artifact reduction.

The estimated true ECG is used for diagnostic purposes, as input to an associated defibrillator or AED. When the estimated true ECG is provided to an AED, the AED can be operated according to its typical modes of operation, which include accepting estimated true ECG data as input, analyzing that ECG data to determine whether it represents a shockable or non-shockable rhythm, and apply defibrillating shock when a shockable rhythm is detected.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

The invention claimed is:

1. An electrocardiogram (ECG) signal processing system for processing an ECG signal of a patient undergoing transport provided by a vehicle, said processing system comprising:
   one or more vehicle motion sensors operably connected to the vehicle and operable to generate one or more signals corresponding to vehicle motion;
   electrodes operable to measure the ECG signal of the patient;
   an output device;
   a processor communicatively coupled to the one or more vehicle motion sensors, the electrodes, and the output device, the processor configured to:
      receive the one or more signals corresponding to the vehicle motion from the one or more vehicle motion sensors and the measured ECG signal from the electrodes,
      process the one or more signals corresponding to the vehicle motion and the measured ECG signal to determine an estimated true ECG signal, and
      output the estimated true ECG signal to the output device.

2. The ECG signal processing system of claim 1 further comprising a CPR motion sensor configured to provide a signal corresponding to motion of the chest of the patient during CPR chest compressions, wherein the processor is communicatively coupled to the CPR motion sensor and further configured to:
   receive the signal corresponding to the motion of the chest of the patient during CPR chest compressions; and
   process the signal corresponding to the motion of the chest of the patient during CPR chest compressions to determine the estimated true ECG signal.

3. A method of calculating an estimated true ECG signal from a patient undergoing transport provided by a vehicle, said method comprising:
   receiving, at a processor, from one or more vehicle motion sensors operably connected to the vehicle and communicatively coupled to the processor, a first input comprising one or more signals corresponding to vehicle motion;

receiving, at the processor, from electrodes communicatively coupled to the processor, a second input comprising a measured ECG signal of the patient;

processing the first input and the second input, by the processor, to determine the estimated true ECG signal; and outputting, by the processor to an output device, the estimated true ECG signal.

4. The method of claim 3 further comprising:

receiving, at the processor, from a CPR motion sensor communicatively coupled to the processor, a signal corresponding to motion of the chest of the patient during CPR chest compressions; and processing the signal corresponding to the motion of the chest of the patient during CPR compressions to determine the estimated true ECG signal.

5. The ECG signal processing system of claim 1 wherein the processor is further configured to:

estimate vehicle motion induced artifacts in the measured ECG signal based on the one or more signals corresponding to the vehicle motion; and remove the estimated vehicle motion induced artifacts from the measured ECG signal to determine the estimated true ECG signal.

6. The ECG signal processing system of claim 5 wherein the processor further comprises a signal combiner configured to subtract the estimated vehicle motion induced artifacts from the measured ECG signal to determine the estimated true ECG signal.

7. The ECG signal processing system of claim 5 wherein the processor is further configured to estimate the vehicle motion induced artifacts in the measured ECG signal based on a linear predictive filter.

8. The ECG signal processing system of claim 7 wherein the processor is further configured to identify the linear predictive filter.

9. The ECG signal processing system of claim 5 wherein the processor is further configured to estimate the vehicle motion induced artifacts in the measured ECG signal based on a non-linear predictive filter.

10. The ECG signal processing system of claim 9 wherein the processor is further configured to identify the non-linear predictive filter.

11. The ECG signal processing system of claim 5 wherein the one or more vehicle motion sensors are operably connected to one or more components of the vehicle and wherein the one or more signals corresponding to the vehicle motion are one or more signals corresponding to motion of the one or more components of the vehicle.

12. The ECG signal processing system of claim 11 wherein the one or more components of the vehicle comprise one or more of a gurney, a vehicle cabin, a vehicle frame, and one or more vehicle suspension components.

13. The ECG signal processing system of claim 12 wherein the processor is further configured to:

receive a signal corresponding to motion of the vehicle cabin and a signal corresponding to motion of the one or more vehicle suspension components, and process the signal corresponding to the motion of the vehicle cabin and the signal corresponding to the motion of the one or more vehicle suspension components to account for a delay in transmission of vibrations from the one or more vehicle suspension components to the vehicle cabin to estimate the vehicle motion induced artifacts in the measured ECG signal.

14. The ECG signal processing system of claim 12 wherein the processor is further configured to:

receive a signal corresponding to motion of the vehicle frame and a signal corresponding to motion of the one or more vehicle suspension components, and process the signal corresponding to the motion of the vehicle frame and the signal corresponding to the motion of the one or more vehicle suspension components to account for relative motion between the vehicle frame and the one or more vehicle suspension components to estimate the vehicle motion induced artifacts in the measured ECG signal.

15. The ECG signal processing system of claim 1 wherein the output device comprises a display.

16. The ECG signal processing system of claim 2 wherein the CPR motion sensor comprises one or more of an accelerometer, a velocity sensor, a displacement sensor, and a force sensor.

17. The ECG signal processing system of claim 1 wherein the vehicle comprises a gurney, an ambulance, or a combination thereof.

18. The method of claim 3 wherein the output device comprises a display.

19. The method of claim 3, wherein the processing the first input and the second input comprises:

estimating vehicle motion induced artifacts in the measured ECG signal based on the one or more signals corresponding to the vehicle motion; and determining the estimated true ECG signal by removing the estimated vehicle motion induced artifacts from the measured ECG signal.

20. The method of claim 19 further comprising determining the estimated true ECG signal by subtracting the estimated vehicle motion induced artifacts from the measured ECG signal.

21. The method of claim 19 further comprising estimating the vehicle motion induced artifacts in the measured ECG signal based on a linear predictive filter.

22. The method of claim 21 further comprising identifying the linear predictive filter.

23. The method of claim 19 further comprising estimating the vehicle motion induced artifacts in the measured ECG signal based on a non-linear predictive filter.

24. The method of claim 23 further comprising identifying the non-linear predictive filter.

25. The method of claim 19 wherein the one or more vehicle motion sensors are operably connected to one or more components of the vehicle and wherein the one or more signals corresponding to the vehicle motion are one or more signals corresponding to motion of the one or more components of the vehicle.

26. The method of claim 25 wherein the one or more components of the vehicle comprise one or more of a gurney, a vehicle cabin, a vehicle frame, and one or more vehicle suspension components.

27. The method of claim 26 further comprising:

receiving a signal corresponding to motion of the vehicle cabin and a signal corresponding to motion of the one or more vehicle suspension components; and estimating the vehicle motion induced artifacts in the measured ECG signal by processing the signal corresponding to the motion of the vehicle cabin motion and the signal corresponding to the motion of the one or more vehicle suspension components to account for a delay in transmission of vibrations from the one or more vehicle suspension components to the vehicle cabin.

28. The method of claim 26 further comprising:

receiving a signal corresponding to motion of the vehicle frame and a signal corresponding to motion of the one or more vehicle suspension components; and estimating the vehicle motion induced artifacts in the measured ECG signal by processing the signal corresponding to the motion of the vehicle frame and the signal corresponding to the motion of the one or more vehicle suspension components to account for relative motion between the vehicle frame and the one or more vehicle suspension components.

29. The method of claim 3 wherein the vehicle comprises a gurney, an ambulance, or a combination thereof.

* * * * *